Nov. 4, 1952 E. S. BOERNER Plant Pat. 1,143
ROSE PLANT
Filed Jan. 17, 1952
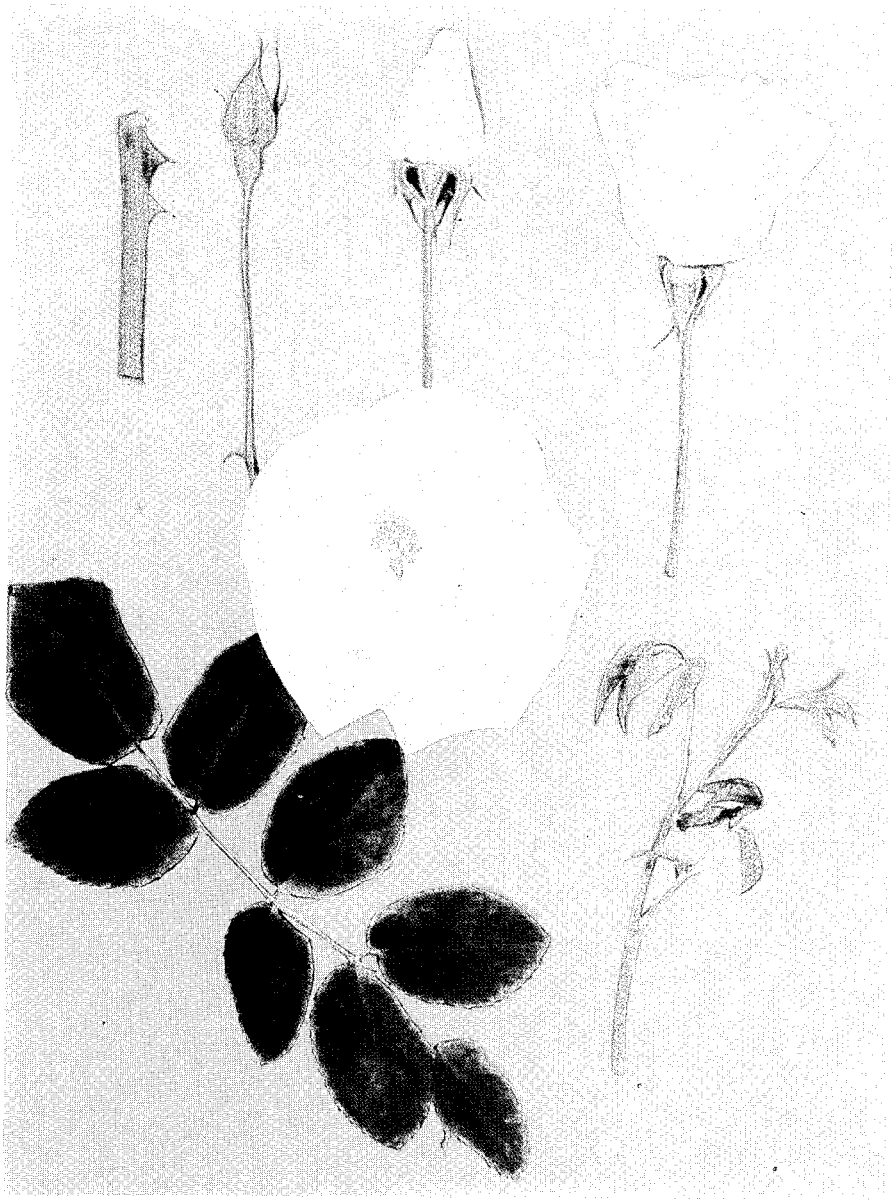
Inventor.
E. S. Boerner
By: Robb & Robb
Attorneys.

Patented Nov. 4, 1952

Plant Pat. 1,143

UNITED STATES PATENT OFFICE 1,143

ROSE PLANT

Eugene S. Boerner, Newark, N. Y., assignor to Jackson & Perkins Company, Newark, N. Y., a corporation of New York Application January 17, 1952, Serial No. 266,821

1 Claim. (Cl. 47—61)

The present invention relates to a new and distinct variety of rose plant of the large-flowered polyantha class, originated by me by crossing the variety "Red Radiance" (unpatented) with the variety "Fashion" (Plant Patent No. 789).

The primary objective in making this cross was to produce a new variety of rose plant of the "Fashion" type, but of larger size and different color, while preserving the hardiness characteristics of both "Fashion" and "Red Radiance." This objective was fully achieved, as evidenced by the fact that my new variety is a taller-growing Radiance rose of the "Fashion" type.

The new variety is still further distinguished from its parents, as well as from all other known varieties of its class, by the following unique and important combination of dominant characteristics:

(1) The particularly clean and sparkling Eosine Pink, overcast with Safrano Pink, color of its blooms;

(2) The floriferousness and hardiness of the new variety which is unusual and much desired in a rose of such color;

(3) The vigorous growth; and (4) The unusual cinnamon fragrance of the blooms.

Asexual reproduction of the new variety by budding at Newark, New York, and at Pleasanton, California, shows that the foregoing characteristics and distinctions come true to form and are established and transmitted through succeeding propagations.

The accompanying drawing shows specimen flowers, foliage, stems and thorns of my new variety in different stages of development.

The following is a detailed description of my new variety, with color terminology in accordance with Ridgway's Color Standards and Nomenclature:

Parentage: Seedling.

*Seed parent.*—"Red Radiance."

*Pollen parent.*—"Fashion."

Classification:

*Botanic.*—Large-flowered polyantha.

*Commercial.*—Floribunda.

*Flower*

(Observations made in the fields at Newark, New York, about mid-morning, early in the month of October.)

Blooming habit: Recurrent—continuous.

Bud:

*Size.*—Medium.

*Form.*—Ovoid; is not affected by wet or hot weather.

*Color.*—When sepals first divide—Spectrum Red, Plate 1. When petals begin to unfurl—Begonia Rose, Plate 1. When half blown: Inside of petals—Eosine Pink, Plate 1, lightly overcast with Orange Pink, Plate 2; reverse of petals—Eosine Pink, Plate 1, lightly overcast with Spinel Pink, Plate 26, and with the lower quarter of the petal washed with Deep Chrome, Plate 3.

*Sepals.*—Slightly branched; "hood" above bud; curl back when petals being to unfurl. Color: inside—Kildare Green, Plate 31; outside—Biscay Green, Plate 17.

*Calyx.*—Shape — pear. Size — small. Aspect—smooth. Odor when rubbed—none. Color—Light Bice Green, Plate 17.

*Peduncle.*—Length—short. Aspect — Rough. Color — Light Bice Green, Plate 17. Strength—erect; slender.

*Opening.*—Opens up well; is not affected by adverse weather conditions.

Bloom:

*Size.*—Large. Average size when fully expanded—3½ inches to 4 inches.

*Borne.*—Several together and in irregular clusters.

*Stems.*—Medium length; strong.

*Form.*—When first open—cupped. permanence—flattens.

*Petalage.*—Double (full but open center). Number of petals under normal conditions—20 to 25.

*Color.*—Center of flower—Eosine Pink, Plate 1, overcast with Orange Pink, Plate 2. Outer petals—Hermosa Pink, Plate 1, lightly overcast with Shrimp Pink, Plate 1. Base of petals (aiglet)—Pinard Yellow, Plate 4. Inside of petals—Eosine Pink, Plate 1, overcast with Safrano Pink, Plate 2, giving a sparkling effect. Reverse of petals—La France Pink, Plate 1. General tonality from a distance—Eosine Pink, Plate 1, overcast with Safrano Pink, Plate 2.

*Discoloration.*—General tonality at end of first day—Eosine Pink, Plate 1, overcast with Orange Pink, Plate 2. Second day—Eosine Pink, Plate 1, lightly overcast with Shrimp Pink, Plate 1. Third day—Hermosa Pink, Plate 1, lightly overcast with Shrimp Pink, Plate 1.

Petals:

*Texture.*—Thick; is not affected by wet or hot weather.

*Appearance.* — Inside — s a t i n y; outside—shiny.

*Form.*—Oval.

*Arrangement.*—Imbricated (regularly arranged shingle-like). Petaloids in center—few; large.

*Persistence.*—Drop off cleanly.

*Fragrance.*—Moderate; Light Cinnamon.

*Lasting quality.*—On the plant and as cut flower—long.

*Genital organs*

Stamens, anthers: Medium size; few.

*Arrangement.*—Regular around styles.

*Color.*—Maize Yellow, Plate 4.

Stamens, filaments (threads):

*Length.*—Medium.

*Color.*—Martius Yellow, Plate 4.

Pollen: Color—Baryta Yellow, Plate 4.

Styles: Columnar; even and medium length; thin.

Stigmas: Color—Pinard Yellow, Plate 4.

Ovaries: All enclosed in calyx.

*Plant*

Form: Bush.

Growth: Vigorous; upright.

Foliage: 5 to 9 leaflets.

*Size.*—Medium.

*Quantity.*—Normal abundance.

*Color.*—New foliage: upper side—Lettuce Green, Plate 5, lightly overcast with Oxblood Red, Plate 1; under side—Cosse Green, Plate 5, overcast with Oxblood Red, Plate 1. Old foliage: upper side—Cress Green, Plate 31; under side—Light Hellebore Green, Plate 17.

*Shape.*—Oval pointed.

*Texture.*—Upper side—glossy; under side—smooth. Ribs and veins—ordinary.

*Edge.*—Slightly serrated (saw-toothed).

*Serration.*—Small.

*Leaf stem.*—Color—Absinthe Green, Plate 31. Under side—prickles.

*Stipules.*—Medium length; slightly bearded.

Wood:

*New wood.*—Color—Yellowish Oil Green, Plate 5. Bark—smooth.

*Old wood.*—Color—Cerro Green, Plate 5. Bark—smooth.

Thorns:

*Thorns.*—Quantity—on main stalks from base and on laterals from stalk—ordinary. Form—flat base; medium length; straight and slightly hooked downward. Color when young—Eugenia Red, Plate 13. Position—irregular.

*Prickles.*—Quantity—on main stalks and on laterals—none.

*Short needles.*—Quantity—on main stalks and on laterals—none.

I claim:

A new and distinct variety of rose plant of the large-flowered polyantha class, substantially as herein shown and described, characterized as to novelty particularly by its relatively taller habit of growth for a Radiance Rose of the type of "Fashion" (Plant Patent No. 789), by its vigorous growth, hardiness and fluoriferousness, by the clean and sparkling predominantly Eosine Pink color, overcast with Safrano Pink, of its blooms, and by the cinnamon fragrance of its blooms.

EUGENE S. BOERNER.

No references cited.